(12) United States Patent
Biedermann et al.

(10) Patent No.: US 8,518,084 B2
(45) Date of Patent: Aug. 27, 2013

(54) CONNECTING ROD WITH EXTERNAL FLEXIBLE ELEMENT

(75) Inventors: Lutz Biedermann, VS-Villingen (DE); Wilfried Matthis, Weisweil (DE); Jürgen Harms, Karlsruhe (DE); Scott Carpenter, Fremont, CA (US); Minh Dinh, Fremont, CA (US); Raghuveer Basude, Fremont, CA (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 1341 days.

(21) Appl. No.: 11/698,237

(22) Filed: Jan. 24, 2007

(65) Prior Publication Data

US 2007/0203446 A1 Aug. 30, 2007

Related U.S. Application Data

(60) Provisional application No. 60/761,850, filed on Jan. 24, 2006.

(51) Int. Cl.
*A61B 17/70* (2006.01)
(52) U.S. Cl.
USPC .......................................... 606/254; 606/259
(58) Field of Classification Search
USPC ................ 606/246, 254–263, 264–278, 279; 403/326, 329
See application file for complete search history.

(56) References Cited

U.S. PATENT DOCUMENTS

| 5,540,688 | A | * | 7/1996 | Navas ............................ 606/266 |
| 5,597,007 | A | * | 1/1997 | Ju ................................. 403/329 |
| 5,672,175 | A | | 9/1997 | Martin |
| 8,157,843 | B2 | | 4/2012 | Biedermann et al. |
| 2003/0109880 | A1 | | 6/2003 | Shirado et al. |
| 2003/0220643 | A1 | * | 11/2003 | Ferree ............................. 606/61 |
| 2004/0165946 | A1 | * | 8/2004 | Areh et al. .................... 403/326 |
| 2004/0236327 | A1 | * | 11/2004 | Paul et al. ....................... 606/61 |
| 2004/0267260 | A1 | * | 12/2004 | Mack et al. ..................... 606/61 |
| 2005/0056979 | A1 | * | 3/2005 | Studer et al. .................. 267/118 |
| 2005/0171540 | A1 | | 8/2005 | Lim et al. |

(Continued)

FOREIGN PATENT DOCUMENTS

DE     103 27 358 A1    1/2005
DE   10 2004 011 685 A1   9/2005

(Continued)

OTHER PUBLICATIONS

International Search Report for EP 07 10 1017, dated May 11, 2007, 7 sheets.

(Continued)

*Primary Examiner* — Jan Christopher Merene
*Assistant Examiner* — Steven Cotroneo
(74) *Attorney, Agent, or Firm* — Christie, Parker & Hale, LLP

(57) ABSTRACT

The present invention concerns a flexible connecting device for implantation into the human or animal body and especially for stabilizing the spine with a first rod, which has at least one flexible middle section and at least two connecting sections. At least one part of the flexible middle section includes an adjustment element, such as a flexible element or a stabilization element, which is arranged outside the cross-section of the first rod and connected to the first rod at a first location.

29 Claims, 5 Drawing Sheets

(56) References Cited

U.S. PATENT DOCUMENTS

| | | |
|---|---|---|
| 2005/0203519 A1 | 9/2005 | Harms et al. |
| 2005/0288672 A1 | 12/2005 | Ferree |
| 2006/0129147 A1 | 6/2006 | Biedermann et al. |
| 2006/0189984 A1* | 8/2006 | Fallin et al. ............... 606/61 |
| 2006/0212033 A1* | 9/2006 | Rothman et al. ............ 606/61 |
| 2008/0033435 A1* | 2/2008 | Studer et al. ............... 606/61 |

FOREIGN PATENT DOCUMENTS

| | | |
|---|---|---|
| DE | 10 2004 018 621 A1 | 11/2005 |
| EP | 0 677 277 A2 | 3/1995 |
| EP | 0 677 277 A3 | 3/1995 |
| EP | 1 574 173 A1 | 9/2005 |
| WO | WO 03/047441 A1 | 6/2003 |
| WO | WO 03/047442 A1 | 6/2003 |
| WO | WO 2004/105577 A2 | 12/2004 |
| WO | WO 2005/030031 A2 | 4/2005 |
| WO | WO 2005/039454 A2 | 5/2005 |
| WO | WO 2005/094704 A1 | 10/2005 |
| WO | WO2005092222 | 10/2005 |

OTHER PUBLICATIONS

Opinion of the extended European Search Report concerning counterpart Application No. EP1810624 dated Jun. 1, 2007, 2 pages.

Non-final Office action for U.S. Appl. No. 11/642,566, mailed Mar. 24, 2009, 7 sheets.

Final Office action for U.S. Appl. No. 11/642,566, mailed Oct. 23, 2009, 10 sheets.

Non-final Office action for U.S. Appl. No. 11/642,566, mailed Jun. 10, 2011, 10 sheets.

Non-final Office action for U.S. Appl. No. 13/425,153, mailed Nov. 9, 2012, 10 sheets.

* cited by examiner

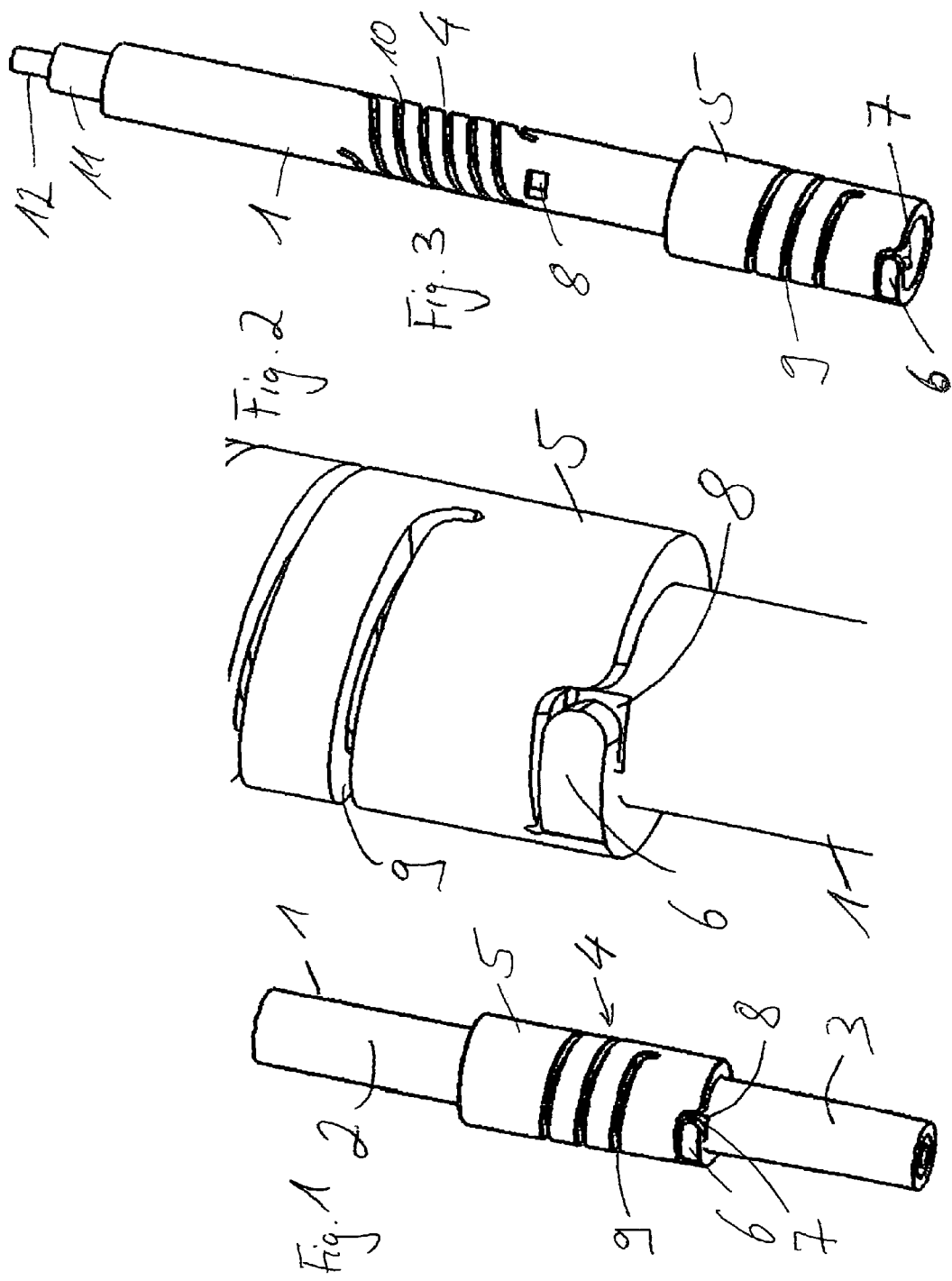

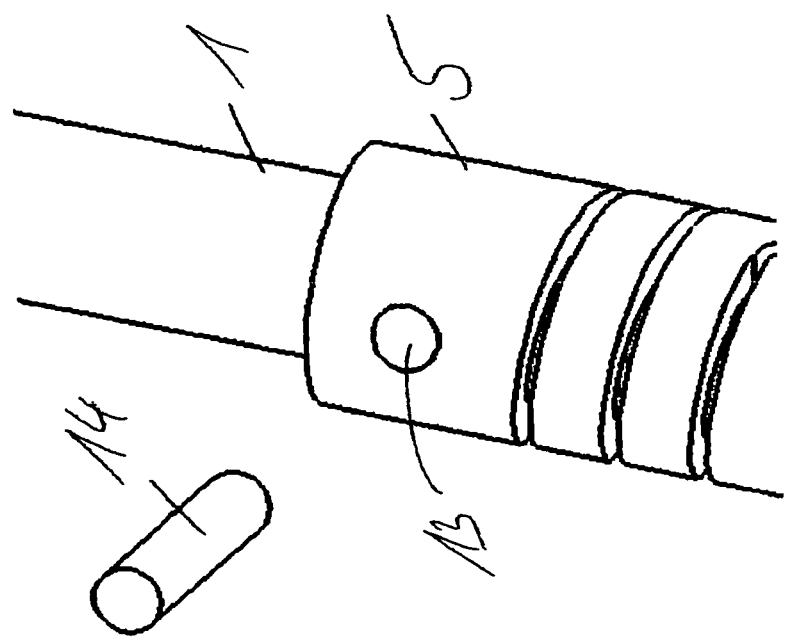

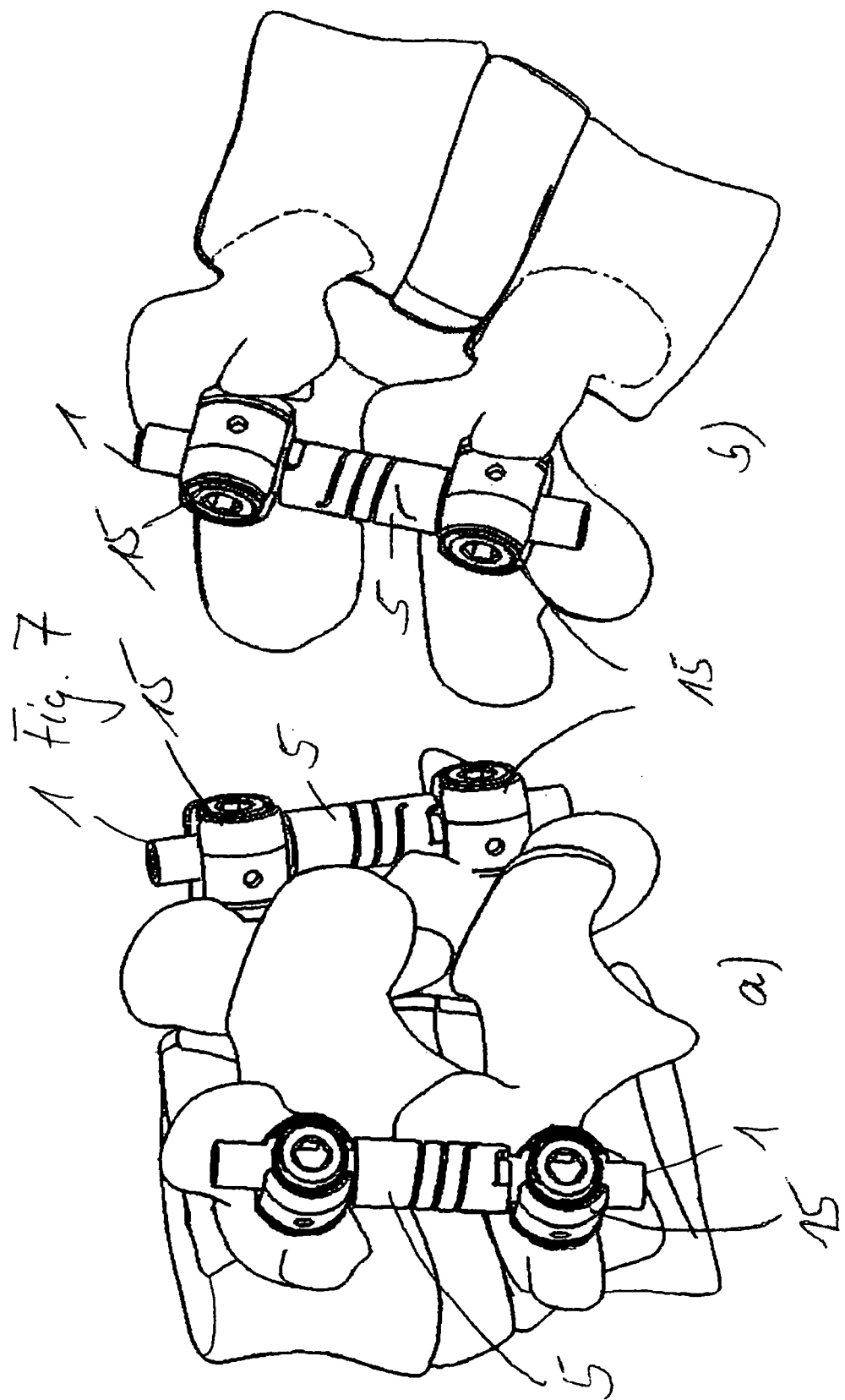

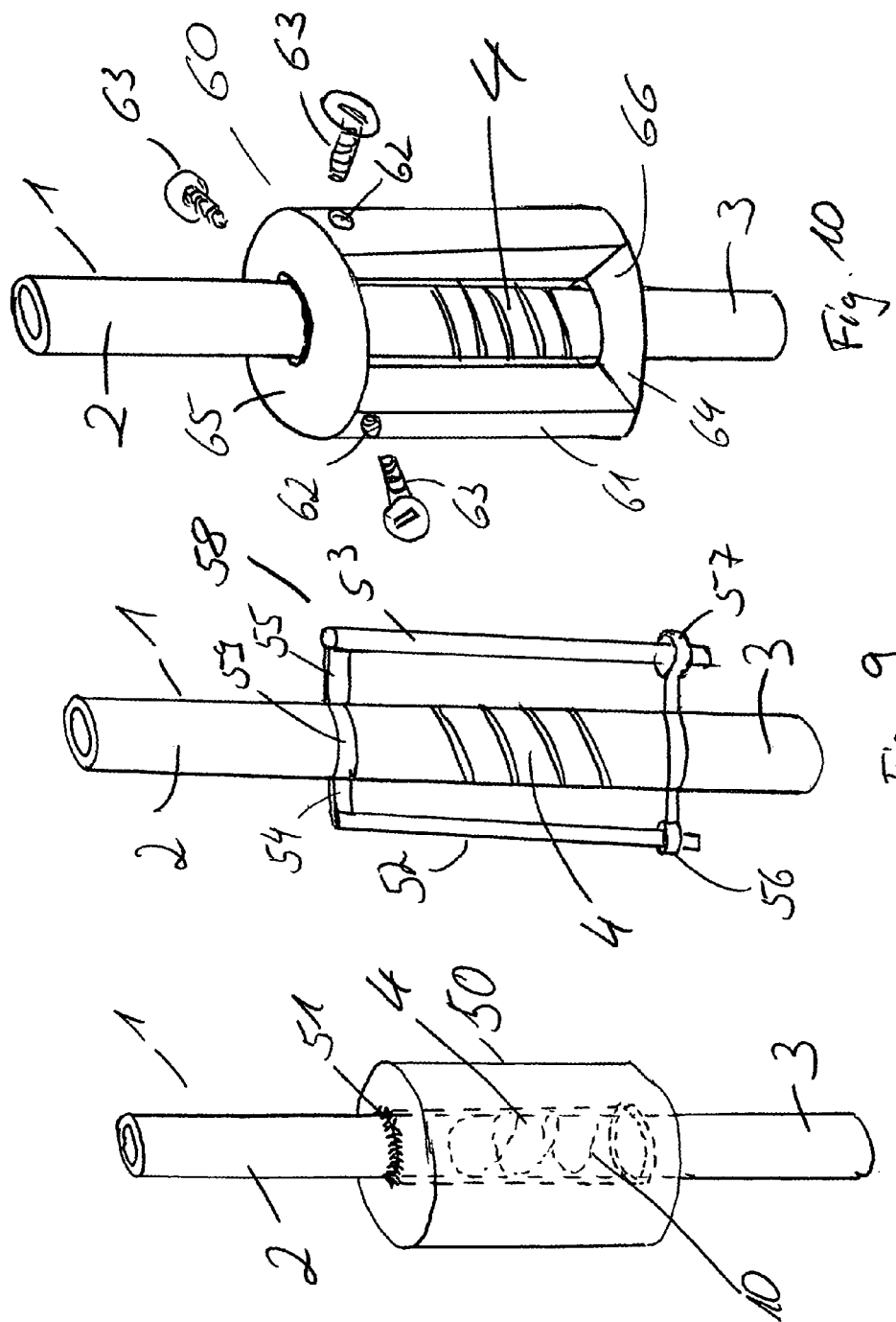

CONNECTING ROD WITH EXTERNAL FLEXIBLE ELEMENT

CROSS-REFERENCE TO RELATED APPLICATION(S)

This application claims priority to and the benefit of Provisional Patent Application No. 60/761,850, filed on Jan. 24, 2006, incorporated by reference herein.

BACKGROUND

The present invention relates generally to a flexible connecting device and to a flexible stabilization system with such a flexible connecting device, especially for use in spinal surgery. Furthermore, the invention also relates to a corresponding modular system.

Flexible stabilization devices for the spine are known. US 2003/0109880 A1 discloses a stabilization system with an elastic rod element, which is provided as a connecting element between two bone anchors, whereby the elastic rod element is formed from a helical spring with narrow threads.

WO 2005/030031 A2 and WO 2005/039454 A2 similarly disclose flexible spinal stabilization systems in which different types of flexible connecting rods are provided between bone anchors. These patent documents propose that flexible connecting rods for achieving flexibility or mobility should have spiral cuts or slits and be combined with core rods in order that both, flexibility and rigidity, or together defined as spring properties, may be adjusted correspondingly.

Similar considerations apply to EP 0 677 277 A2, which also describes a dynamic or flexible stabilization device, especially for the spine, in which, again, a rod with cuts or a spiral slit is provided as a flexible connecting device. A viscoelastic material may be filled into the cavity of the part with the slit.

WO 03/047442 A1, in turn, proposes a damping element and a device for stabilizing adjacent vertebral bodies. In a first embodiment, two elastic elements are coaxially arranged one inside the other and are connected to two connecting elements. One elastic element is a spirally slit tube and the other is a core element. In a second embodiment, a tubular spring element with a spiral arrangement of slits has a one-piece connector and a receiving opening for adjacent flexible elements. A second spring element is provided as a core element within the first spring element.

US 2003/0220643 A1 similarly discloses a flexible stabilization device for the spine, whereby, again, spiral-spring-like connecting rods are provided between pedicle screws or bone anchoring elements. US 2003/0220643 A1 additionally proposes providing the spiral-spring-like connecting rods with sleeves which act as spacers between the pedicle screws to prevent too much deformation or mobility.

WO 2004/105577 A2, in turn, describes a spinal stabilization system in which differently shaped, flexible connecting rods are used between the bone anchors. They consist of metal strips wound spirally into tubes or of structures braided from metal fibers. Also described are spring elements which are inserted between rods or spirally slit cylindrical tubes with and without cores.

Although some of the above-described prior art stabilization systems have very good properties, the goal remains to create a flexible connecting device for arrangement between bone and vertebral anchors, that replicates the complex, mechanical properties of the spine. Such a device ideally provides adequate support as well as retention of mobility in damaged spinal regions, and is easy to manufacture and easy to manipulate by the surgeon during surgery.

SUMMARY

According to a first aspect, the present invention is a flexible connecting device for implantation into the human or animal body, especially as a connecting element or connecting rod for stabilizing the spine. The flexible connecting device of the invention comprises a first rod that has at least one flexible section and at least two connecting sections, the latter of which are adapted for attachment to anchoring devices to be secured to the human or animal body, especially anchoring elements for the vertebrae of the spine. Such a flexible connecting device facilitates stabilization by load accommodation combined with simultaneous mobility via the flexible section. Thus far, a flexible connecting device as described above corresponds to known flexible connecting rods, for example for use in stabilization systems for the spine.

The flexible connecting device of the present invention features, in addition to the above-described first rod, an attachment which extends along at least a part of the flexible section of the first rod. More precisely, the attachment is a property adjustment element, located outside the rod cross-section, that can affect the flexibility and stabilization properties of the device. In one embodiment, the property adjustment element forms an outer element connected to the first rod in at least one location such that it cannot be displaced axially.

In the following, the property adjustment element is described as a flexible element or a stabilization element, depending on its primary function. A flexible element, while having a certain flexibility and thus mobility, and especially reversible deformability, can additionally take on stabilization functions, which are inherent in the design. For example, a flexible element arranged outside the rod cross-section may provide stabilization with respect to specific loads, for example shearing loads, while other loads like bending forces lead to a deformation of the flexible element. Thus, a flexible element being primarily flexible is not restricted to be merely flexible, but can provide stabilization in specific load cases.

The stabilization element, while primarily stiff and rigid, may exhibit a minor degree of flexibility or elasticity under certain loads. Moreover, such an element can facilitate a certain degree of reversible deformability or mobility of the first rod without being significantly deformed itself, e.g., in order to effectuate the flexible or dynamic properties of the flexible connecting device of the invention. This can occur in such a manner that, in certain directions of movement or in certain forms of movement, the stabilization element provides the first rod with sufficient scope of movement, without itself having to be deformed or moved. For example, due to the connection of a stabilization element arranged outside the rod cross-section to the first rod in only one connecting location, the first rod may be compressed in an axial direction or bended about axes perpendicular to the longitudinal axis, while the essentially stiff outer element is neither loaded nor deformed during the motion of the first rod. Thus, the design of the outer element is such that the first rod can perform specific movements without affecting the outer element. Other movements, however, can be prevented by the outer element such as deformation or movement due to shearing loads.

The mechanical properties of the flexible connecting device are affected by the shape of the first rod or primary rod and any core optionally provided therein. The arrangement of a flexible element or a stabilization element outside the rod cross-section facilitates additional adjustment of the mechanical properties of the flexible connecting device. Thus, the flexible connecting device of the invention is particularly suited for use in a modular system in which the surgeon can make an adjustment to the mechanical properties of the flexible connecting device by selecting the appropriate individual components, namely the flexible element or stabilization element. The modular concept allows for easy manufacturing and moreover facilitates simplified and smaller inventory for industry (including manufacturing and sales departments) and hospitals.

Moreover, through the external arrangement, the connecting technique between flexible element or stabilization element on the one hand and the first rod on the other hand is markedly simplified. Further, deliberate arrangement of the flexible element or stabilization element solely in the flexible section of the first rod or a part thereof can allow particularly accurate adjustment of the mechanical properties of the flexible connecting device, such as reversible deformability, extensibility, etc.

The flexible element or stabilization element may be formed as a rod, strip, partial cylinder, especially a half-shell or similar, or as a cylindrical-tubular body, as described in further detail below. These simple geometrical forms also facilitate simple connection between the flexible element or stabilization element on the one hand and the first rod on the other.

Similar to the flexible section of the first rod, the flexible element can achieve its flexibility or reversible deformability both by design, such as cross-sectional and/or wall thickness reductions, and/or the provision of material recesses and/or by the choice of a correspondingly flexible material. Consequently, various possibilities for achieving flexibility or reversible deformability are available for the various applications and areas of application.

Preferred, however, is the formation of the flexible element as a cylindrical-tubular body that has at least one slit and/or grooved material recess, which is especially provided spirally or helically about the longitudinal axis of the cylindrical-tubular body. The slit and/or grooved material recess can pass completely through the wall thickness of the cylindrical-tubular body (slit) or a residual wall thickness may remain (groove).

Through such a design, the possibility of axial extension and/or compression, torsion about the longitudinal axis, and/or bending about a radial axis (transverse axis) is created, such that all movements are possible in all spatial directions. Correspondingly, it is also preferred that the flexible section of the first rod is formed in a similar way.

It is advantageous if the flexible element or stabilization element is provided exclusively in the flexible section(s) of the first rod, since only these sections require corresponding adjustment of the mechanical properties via the flexible element or stabilization element.

This also makes it possible for the flexible element or the stabilization element to be connected to the first rod in a section between the connecting section and the flexible section of the first rod for which purpose preferably positive and/or non-positive joints are provided and/or frictional connections and/or material connections.

The positive and/or non-positive joints can, for example, be formed by catches, such as hooks or projecting noses that engage with openings, pins that also engage with corresponding openings, or screw connections with screws in threaded holes.

A preferred embodiment of catches consists of, for example, at the flexible element or stabilization element, an inwardly projecting protuberance that engages with a recess of the first rod, said protuberance especially being arranged on a spring-loaded flap or bending flap.

Thus, in a simple but effective manner, a connection can be achieved between the flexible element or stabilization element on the one hand and the first rod on the other. Such a connection prevents an axial displacement of the flexible element or stabilization element relative to the first rod at the connection in the direction of the longitudinal axis of the first rod.

Preferably, only a single connecting location, especially in a plane perpendicular to the longitudinal axis, is provided between the flexible element or the stabilization element on the one hand and the first rod on the other. This makes it possible for the first rod to extend in the axial direction independently of the flexible element or stabilization element. Correspondingly, the flexibility or reversible mobility or deformability of the first rod in the axial direction is not influenced by the flexible element or stabilization element and the adjustment of the mechanical properties or a stabilization function becomes effective only as regards the remaining types of deformation or movement.

The first rod may preferably be formed from a cylindrical solid body or cylindrical-tubular body in which preferably additional core elements in the form of one or several second rods may be provided that may be arranged coaxially with each other.

The second rod may, in the same manner as the first rod, have one or more flexible sections or be formed such that it is overall flexible or reversibly deformable.

The second rod may preferably, like the flexible element or the stabilization element, be connected to the first rod at just one location, such that the rods may be deformed or moved independently of each other in the axial direction. Therefore, the connection between the first rod and the second rod(s) is preferably provided in the end section of the rods.

The first and/or second rod may, as already mentioned, be shaped with its flexible section similar to that of the flexible element. However, in order that an additional stabilization function may be obtained, especially with regard to transverse forces or flexural stress, the threads of the spiral slit and/or grooved material recesses of adjacent components, namely the flexible element and the first rod, or the first rod and the second rod may for example be formed such that the windings and threads run in opposite directions or are mirror-symmetrical.

In addition, the helical or spiral shapes of the flexible section or the flexible element may be characterised by the fact that, for example, a double helix is used and that the radius or diameter is enlarged or reduced, such that the spiral section has the shape of a waist, stomach or barrel.

The first rod, a second or third rod, or other additional rods and the flexible element may be made of a flexible material, especially a bio-compatible plastic or metal. Preferred is the use of a super- or pseudo-elastic material and here especially the use of nitinol, a nickel-titanium alloy. A material of this kind possesses the special properties that are advantageous for the aforementioned application.

Suitable plastics include polyethylene (PE) and polytetrafluoroethylene (Teflon), as well as polyethylene terephthalate (PET).

Preferably, the first rod and/or the outer element are made of nitinol and a second or other core rods are made of plastic.

To keep ease of manufacture as simple as possible and also to facilitate convenience during surgery, the flexible element, the first rod, the second rod and/or any additional rods, may each be formed as one piece.

According to a second aspect of the present invention, a connecting element of the invention, is used in a flexible stabilization system, especially for the spine, in which the flexible connecting device serves to connect bone anchors, so-called anchoring elements, which are attachable to vertebrae of the spine. Both single-segment and multi-segment implantations are possible. A segment is meant here to be two adjacent vertebrae with an intervertebral disc arranged between them. A multi-segment implantation therefore means the connection of more than two vertebral bodies with the flexible connecting device.

The anchoring elements can be pedicle screws, which may be formed as polyaxial screws in order that arbitrary alignment of the connecting element to the anchoring screw may be ensured.

According to a third aspect of the present invention, not only the stabilization system but also the flexible connecting device is formed as a modular system, which enables the surgeon to adjust the implant to the patient concerned during the intervention, by, for example, exchanging the flexible element or the stabilization element of the flexible connecting device.

BRIEF DESCRIPTION OF THE FIGURES

Further advantages, characteristics and features of the present invention are apparent from the following detailed description of embodiments using the enclosed drawings, which are shown in purely schematic form.

FIG. 1 shows a three-dimensional representation of a connecting element of the invention;

FIG. 2 shows an enlarged representation of the section from FIG. 1;

FIG. 3 shows a three-dimensional representation of the connecting element from FIGS. 1 and 2 in the disassembled state;

FIG. 6 shows a three-dimensional representation of an alternative connection between flexible element and the first rod of a connecting element of the invention;

FIGS. 7a and 7b show two three-dimensional representations a) and b) of stabilization systems of the invention.

FIG. 8 shows a three-dimensional representation of an alternative embodiment of the connecting element of the invention;

FIG. 9 shows a three-dimensional representation of another alternative connecting element of the invention; and FIG. 10 shows a three-dimensional representation of yet another embodiment of the connecting element of the present invention.

DETAILED DESCRIPTION

Figure 5:
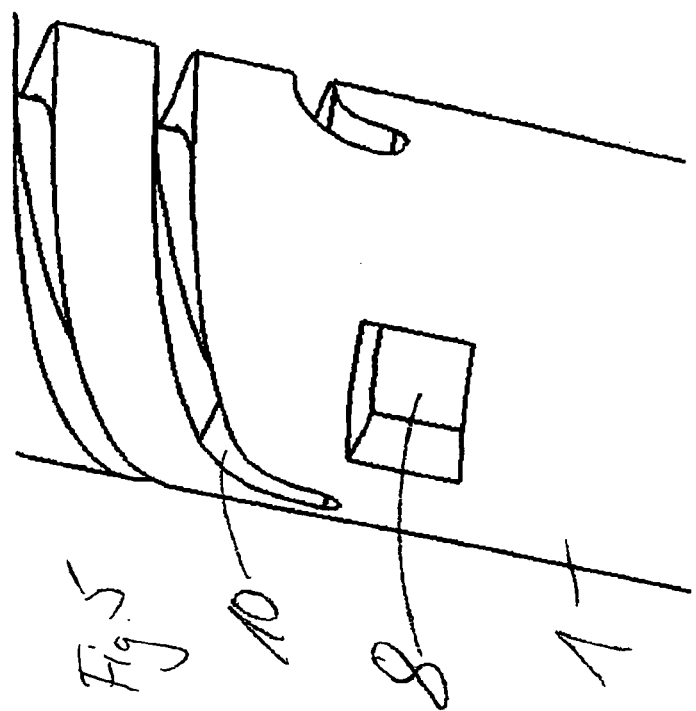
FIG. 5 shows a three-dimensional detailed view of the first rod of connecting element from FIG. 1.

FIGS. 1-3 show a three-dimensional representation of a flexible connecting device of the invention with a first rod 1 and a property adjustment element, such as a flexible element 5. The first rod has a flexible section 4 located between two connecting sections 2 and 3, the latter serving to connect the first rod 1 to the elements to be connected, such as pedicle screws for attachment to the spine.

In the embodiment shown in FIG. 1, the first rod is formed by a cylindrical tube. The connecting sections 2 and 3 form smooth sections of the first rod 1 and are suitable for arrangement in pedicle screws or especially polyaxial screws.

The force transmission between the elements to be connected, such as pedicle screws, proceeds via the first rod 1 into which the force is introduced or extracted directly via the connecting sections 2 and 3.

The flexible section 4 (see FIG. 3) extends between the connecting sections 2 and 3 of the first rod 1. In the illustration of FIG. 1, the flexible section 4 is covered by an additional flexible element 5.

Flexible element 5 is formed as a cylindrical tube, which is arranged coaxially with the first rod 1 and surrounds its flexible section 4.

Flexible element 5 has a slit 9 that completely penetrates the wall of the flexible element 5. The slit 9 has a screw shape or helical shape that permits extension or compression of the flexible element 5 in the axial direction. The slit 9 also permits torsional rotation or bending about a radial rotary axis.

At least one end of the flexible element 5 has a connecting component 6, 7 for connecting to the first rod 1. The connecting component 6, 7 includes a spring-loaded flap 6, which is defined by a gap extending into the flexible element 5 from the end of the flexible element 5. At a free end of the spring-loaded flap 6, an inwardly projecting lug 7, also called a protuberance, projects into an opening 8 in the first rod 1 to connect the flexible element 5 to the first rod 1. A positive joint connection is thus formed, although the connection may be non-positive.

The flap 6 may be capable of flexing outwardly to allow the lug 7 to pass over the first rod 1. The spring-loaded flap 6 is formed such that the projecting lug 7 enters into the opening 8, also called a recess, like a spring. In the unloaded state, the spring-loaded flap 6 is aligned with the cylindrical-tube body of flexible element 5. Alternatively, the flap 6 is not formed as a spring-loaded flap, but rather is formed as a bending flap. After positioning the flexible element 5 over the flexible section 4 of the first rod 1, the projecting lug 7 of the bending flap 6 may be forced into the opening 8 of the first rod 1 by bending of the bending flap 6.

FIG. 2 shows a magnified representation of the connection between the flexible element 5 and the first rod 1, with the connecting component 6, 7 engaging the opening 8, as described above.

In FIGS. 1 and 2, only a single connecting location is provided at the lower end of the flexible element 5. This leads to the flexible element 5, despite axial compression or extension of the first rod 1, not being loaded in the axial direction since the first rod 1 can move freely in a through-hole of the tubular flexible element 5 and only one connection is present between the flexible element 5 and the first rod 1. That is, the single connection is formed by the flap 6 and the projecting lug 7 arranged thereon, and the engagement of the projecting lug 7 in the opening 8.

Alternatively, at the two opposite ends of the flexible element 5, corresponding connections may be provided such that, in the event of axial loading of the first rod 1, the flexible element 5 is also loaded in the axial direction and is extended or compressed according to the axial load.

If only one connection is provided, as shown in FIGS. 1 and 2, the flexible element essentially helps to facilitate or generally influence bending about radial axes, i.e., rotary axes perpendicular to the longitudinal axis of the first rod 1, or to limit shearing transverse to the longitudinal axis of the rod. In the latter case, the flexible element 5 serves as a stabilizing element with regard to the shearing.

FIG. 3 shows a three-dimensional representation of the individual components of a preferred embodiment of the connecting element of the invention in accordance with FIGS. 1 and 2 in an exploded state.

It may first be seen in FIG. 3 that the flexible element 5 is pushed over the first rod 1 during assembly and, provided the projecting lug 7 at the bending or spring-loaded flap 6 does not engage with the opening 8, can be displaced along the longitudinal axis.

Further, FIG. 3 shows the flexible section 4 of the first rod 1, which also is formed with a helical, spiral or screw-shaped slit 10.

As shown by FIGS. 1 and 3, the windings of the slit 9 of the flexible element 5 and the windings of the slit 10 of the flexible section 4 of the first rod are helical and are designed such that they extend in opposite directions or are mirror-symmetrical to each other. Thus, shear forces transverse to the longitudinal axis of the rod can be readily accommodated by the flexible connecting device, while, at the same time, bending about rotary axes perpendicular to the longitudinal axis of the rod is possible, even if the property adjustment element influences the bending.

Superimposing flexible element 5 over flexible section 4 permits adjustment of the mechanical properties of the device, including flexibility or mobility, damping, extensibility, etc. Modularity of the flexible connecting device, by providing several different types of rods and property adjustment elements that can be readily assembled, permits targeted adjustment of the mechanical properties of the flexible connecting device to the requirements of the application concerned.

Furthermore, it may be seen from FIG. 3, that the first rod 1 may be formed as a cylindrical tube. A second rod 11 and a third rod 12 are provided within the first rod 1, with the rod 11 formed as a cylindrical tube in which the cylindrical solid rod 12 is arranged. Rods 11 and 12 are formed preferably to be flexible or elastic or generally deformable, such that the flexible connecting device overall has a flexible and deformable structure. The second rod 11 and the third rod 12 may preferably be made of a plastic material that is inherently sufficiently elastic or flexible, or generally reversibly deformable. Alternatively, the rods 11 and 12 may be made of a metallic material, which has corresponding elastic properties, or especially pseudo-elastic or super-elastic properties, such as nitinol.

Also, the first rod 1 and the flexible element 5 may be made of elastic or flexible or generally reversibly deformable materials, for which the pseudo-elastic or super-elastic material nitinol is especially suitable, which is an alloy of nickel and titanium.

Figure 4:
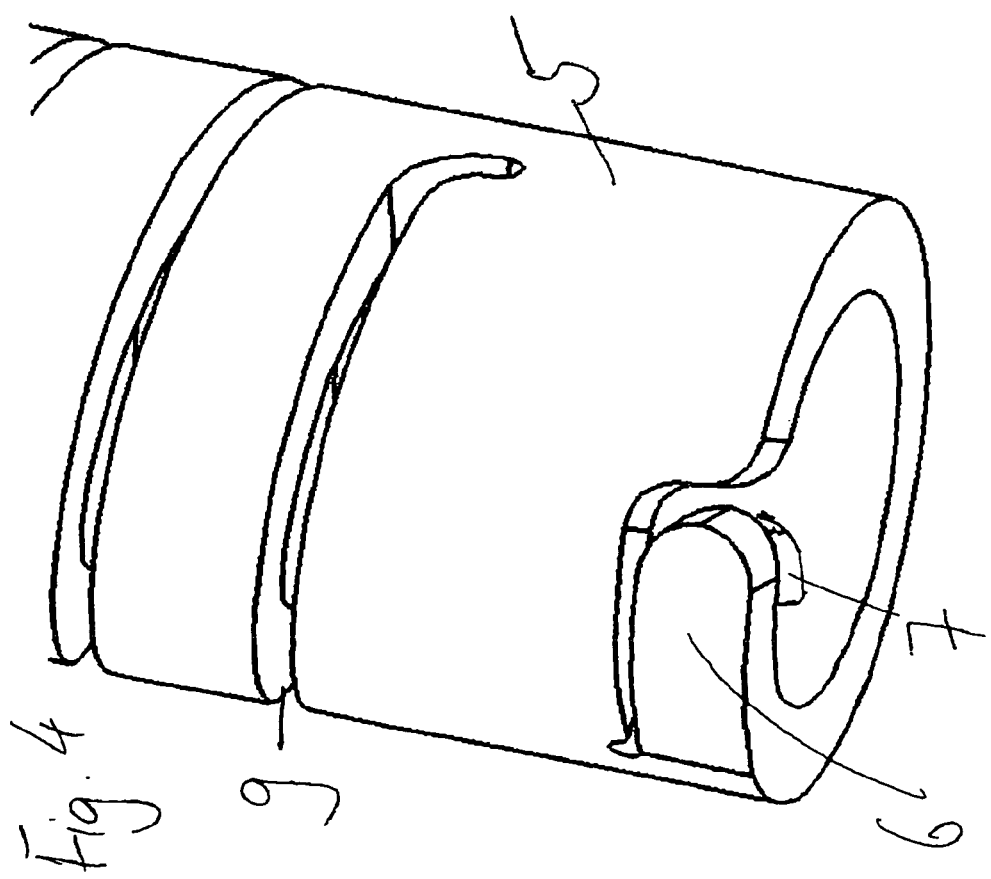
FIG. 4 shows a three-dimensional detailed view of the flexible element of connecting element from FIG. 1.

FIGS. 4 to 6 show two different possibilities for connecting the flexible element 5 to the first rod 1. While FIGS. 4 and 5 detail the positive connection as represented in the embodiment of FIGS. 1 to 3, FIG. 6 shows a further alternative of a positive connection effected by connecting pins 14. To form this connection, corresponding pin 14 is pushed into two aligned openings of the flexible element 5 and the first rod 1, such that the flexible element 5 is immobilized relative to the first rod 1. FIG. 6 shows such an opening 13 of the flexible element 5. The underlying opening of the first rod 1 cannot be seen in the representation in FIG. 6.

Aside from the illustrated connecting techniques for the connection between flexible element 5 and first rod 1, other suitable connecting techniques are possible, such as screw connections or the like. In a screw connection, for example, the embodiment of FIG. 6 would include threads on the pin 14 and the corresponding threads on both the opening 13 of the flexible element 5 and the opening of the first rod 1.

Generally, any connecting technique, including non-positive frictional and material connecting techniques may be used to connect the flexible element 5 and the first rod 1 of the connecting element of the invention.

FIGS. 7a and 7b show the application of stabilization systems of the invention comprising of polyaxial-pedicle screws 15, which are screwed into the vertebrae of the spine, and of flexible connecting devices. In the embodiments shown, between each of two polyaxial screws 15 is provided a flexible connecting device with a flexible section in the middle, around which an outer flexible element is arranged. The flexible section of the flexible connecting device or the element arranged outside the cross-section of the flexible section may abut at the heads of the pedicle screws or may be spaced apart, preferably in the order of magnitude of tenths of a millimetre to several millimeters. The flexible connecting device corresponds to the embodiment as represented in FIGS. 1 to 3.

The connecting sections 2 and 3 of the first rod 1 are received within the screw heads corresponding to the polaxial-pedicle screws 15 and fixed in place. The use of the polyaxial-pedicle screws makes it possible, to a certain extent, to freely orient the longitudinal axis of the first rod 1 of the flexible connecting device of the invention relative to the longitudinal axis of the pedicle screws 15. All types of pedicle screws having the corresponding properties may serve as the polyaxial screws. Although polyaxial screws are preferred, additionally all other pedicle screws or generally known anchoring elements may conceivably be used for attachment to the connecting sections 2 and 3 of the flexible connecting device.

FIGS. 8 to 10 show alternative embodiments of the present invention. In the embodiment shown in FIG. 8 a stabilization element 50 is disposed at the first rod 1 instead of the flexible element 5 shown in FIG. 1. The first rod 1 is identical to that one of the embodiment of FIG. 1. Accordingly the numerals with respect to the first rod 1 are identical to that of FIG. 1.

Stabilization element 50 is formed as a cylindrical-tube in which the first rod 1 is inserted such that the flexible section 4 of the first rod 1 is covered by the stabilization element 50. In order to allow limited bending of the first rod 1, the inner diameter of the through-hole of stabilization element 50 is greater than the outer diameter of the first rod 1. The device in FIG. 8 improves stabilization because the stabilization element improves shearing properties and limits bending of the first rod.

The stabilization element 50 is fixed to the first rod 1 by a circumferential joint weld 51 which surrounds the first rod 1 in the shape of a ring. Since first rod 1 and stabilization element 50 are only connected at a single connecting location at the upper end of stabilization element 50, axial compression or elongation of the first rod 1 is possible FIG. 9 shows a further embodiment of a stabilization element 58 comprising a strip 52 and a cylindrical bar 53. The upper ends of the strip 52 and the bar 53 are immovably fixed to the first rod 1 by ligaments 54 and 55 firmly connected to the first rod 1. The lower ends of the strip 52 and the bar 53 are guided by rings 56 and 57, respectively, which are also firmly attached to the first rod 1. Since the rings 56 and 57 are not firmly fixed to the strip 52 or the bar 53, respectively, the flexible connecting device can be compressed in the axial direction without interaction of the strip 52 or the bar 53. However, the stabilization element comprising the strip 52 and the bar 53 provides stabilization with respect to bending of the first rod 1 dependent on the amount of gap between the strip/bar and the rings. Although, the stabilization element 58 of FIG. 9 comprises a strip 52 and a bar 53 it is also possible to only comprise either strips or bars.

FIG. 10 shows a further embodiment of a flexible connecting device of the present invention having a first rod 1 that is similar to the first rods in the embodiments of FIGS. 1, 8 and 9. Accordingly identical numerals are used for designating corresponding components.

The flexible element 60 shown in FIG. 10 is formed by a partial cylinder 61 which comprises openings 66 in the jacket wall extending from an upper ring plate 65 to a lower ring plate 64. The partial cylinder 61 is fixed to the first rod 1 by screw connections. The screws 63 of the screw connections are engaged within holes 62 of the partial cylinder 61 so as to allow the threaded shafts of the screws 63 to cooperate with threaded holes of the first rod 1 (not shown). Thus, the connection of the flexible element 60 with the first rod 1 is established in the upper part of the partial cylinder 61. Since the flexible element 60 and the first rod 1 are not connected at the lower end opposite to the connecting area, the first rod 1 can be compressed or elongated independently in the axial direction. Due to the openings 66 in the jacket wall, the design of the element 60 is such that an inherent flexibility, e.g. with respect to bending forces, is given, similar to the flexible element 5. Contrary to that, the stabilization elements 50 and 58 of the embodiments shown in FIGS. 8 and 9 have a design predominantly providing stability.

From the embodiments shown in FIGS. 1, 8, 9 and 10 it also becomes evident that different connecting techniques for connecting the flexible element or stabilization element to the first rod 1 can be used.

While in the embodiment shown in FIG. 1 the flexible element 5 is connected to the first rod 1 by positive locking, the stabilization element 50 of the embodiment shown in FIG. 8 is connected to the first rod 1 by a material connection in the form of a welding.

Further, the ligaments 55 and 54 of the embodiment shown in FIG. 9 are attached to the first rod 1 by a ring 59 surrounding the first rod 1 circumferentially in a non-positive frictional manner.

In addition, the screw connections 63 of the embodiment shown in FIG. 10 can be seen as a combination of positive and non-positive connecting techniques, wherein the tightening forces of the screws provide the non-positive part while the engagement of the screw shafts in the threaded holes can be seen as form fit.

What is claimed is:

1. A flexible connecting device for implantation into a human or animal body comprising:
   a first rod having a longitudinal axis, the first rod comprising a flexible middle section located between two connecting sections, the two connecting sections adapted for attachment to anchoring devices to be secured to the human or animal body; and
   an adjustment element having a first end and a second end and extending along and located outside an axially extending part of the flexible middle section of the first rod, wherein the first end of the adjustment element is connected to the first rod at a first location such that the adjustment element is axially immovable relative to the first rod at the first location, and a second end of the adjustment element opposite to the first end is free of connections to permit movement of the first rod at a second location relative to the adjustment element
   wherein at least one of the two connecting sections of the first rod is exposed and has a constant cross-section along the longitudinal axis for direct attachment to an anchoring device.

2. The flexible connecting device of claim 1, wherein the adjustment element is a flexible element or a stabilization element formed as a rod, strip, partial cylinder or cylindrical-tubular body.

3. The flexible connecting device of claim 2, wherein the adjustment element comprises a flexible element having a cross-section reduction, a wall thickness reduction, material recesses, flexible deformable material or reversibly flexible deformable material.

4. The flexible connecting device of claim 1,
   wherein the adjustment element is a flexible element formed as
   a cylindrical-tubular body having at least one slit or grooved material recess for obtaining mobility in axial extension or compression, torsional rotation or bending about a radial axis.

5. The flexible connecting device of claim 4, wherein the slit or grooved material recess is provided spirally or helically about a longitudinal axis of the adjustment element.

6. The flexible connecting device of claim 4, wherein the flexible middle section of the first rod has a cross section reduction, a wall thickness reduction, material recesses or flexible material.

7. The flexible connecting device of claim 6, wherein the flexible middle section of the first rod has at least one helical or screw type slit or grooved material recess for obtaining mobility in axial extension or compression, torsional rotation or bending about a radial axis.

8. The flexible connecting device of claim 7, wherein the slit or grooved material recess of the flexible element is provided spirally or helically about a longitudinal axis of the adjustment element and windings of the slit or grooved material recess of the first rod run in opposing directions and/or are mirror symmetrical to the windings of the adjustment element.

9. The flexible connecting device of claim 1, wherein the adjustment element is provided only over the flexible middle section of the first rod.

10. The flexible connecting device of claim 1, wherein the adjustment element is connected to the first rod at one end of the adjustment element and at one end of the flexible middle section of the first rod.

11. The flexible connecting device of claim 1, wherein the adjustment element is connected to the first rod by a positive connection.

12. The flexible connecting device of claim 1, wherein the adjustment element is connected to the first rod by a non-positive connection.

13. The flexible connecting device of claim 1, wherein the adjustment element has at least one inwardly projecting protuberance that engages with a recess of the first rod.

14. The flexible connecting device of claim 13, wherein the protuberance is located on a spring-loaded flap or a bending flap.

15. The flexible connecting device of claim 1, wherein one or more pins or screws are accommodated in corresponding openings of the adjustment element and the first rod for connecting the adjustment element to the first rod.

16. The flexible connecting device of claim 1, wherein a single connection between the adjustment element and the first rod extends in a plane perpendicular to a longitudinal axis of the adjustment element.

17. The flexible connecting device of claim 1, wherein the first rod comprises a cylindrical solid body or a cylindrical-tubular body.

18. The flexible connecting device of claim 1 further comprising:
a second rod coaxial to and provided within the first rod.

19. The flexible connecting device of claim 18, wherein the second rod has a cylindrical solid body or a cylindrical-tubular body.

20. The flexible connecting device of claim 19, wherein the second rod is connected to the first rod at only one location.

21. The flexible connecting device of claim 20, wherein at least one of the first rod, the second rod and the adjustment element is made of nitinol.

22. The flexible connecting device of claim 21, wherein the first rod and the adjustment element are made of nitinol and the second rod is made of plastic.

23. The flexible connecting device of claim 22, wherein the second rod comprises polyethylene, polytetrafluoroethylene, or polyethylene terephthalate.

24. The flexible connecting device of claim 18, wherein the adjustment element, the first rod and the second rod are each formed as one piece.

25. The flexible connecting device of claim 1, wherein the flexible middle section has greater flexibility than each of the two connecting sections.

26. The flexible connecting device of claim 1, wherein the flexible middle section and the adjustment element are axially movable relative to each other at a location other than the first location.

27. A stabilization system for the spine comprising:
a flexible connecting device comprising:
   a first rod having a longitudinal axis, the first rod comprising a flexible middle section located between two connecting sections; and
   an adjustment element having a first end and a second end and extending along and located outside an axially extending part of the flexible middle section of the first rod, the first end of the adjustment element being connected to the first rod at a first location such that the adjustment element is axially immovable relative to the first rod at the first location, and a second end of the adjustment element opposite to the first end being free of connections to permit movement of the first rod at a second location relative to the adjustment element; and
two anchoring elements configured to be connected respectively to the two connecting sections of the flexible connecting device and connectable to a vertebrae of the spine;
wherein at least one of the two connecting sections of the first rod is exposed and has a constant cross-section along the longitudinal axis for direct attachment to one of the two anchoring elements.

28. The stabilization system of claim 27, wherein the anchoring elements are pedicle screws.

29. The stabilization system of claim 28, wherein the anchoring elements are polyaxial screws.

* * * * *

UNITED STATES PATENT AND TRADEMARK OFFICE
CERTIFICATE OF CORRECTION

PATENT NO.       : 8,518,084 B2                              Page 1 of 1
APPLICATION NO.  : 11/698237
DATED            : August 27, 2013
INVENTOR(S)      : Biedermann It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,531 days.

Signed and Sealed this
Twenty-seventh Day of January, 2015

Michelle K. Lee
*Deputy Director of the United States Patent and Trademark Office*